United States Patent [19]

Turner et al.

[11] Patent Number: 5,544,218
[45] Date of Patent: Aug. 6, 1996

[54] THIN FILM SAMPLE SUPPORT

[75] Inventors: D. Clark Turner; Andrew J. Nielsen; Raymond T. Perkins; Michael Madden, all of Orem, Utah

[73] Assignee: Moxtek, Inc., Orem, Utah

[21] Appl. No.: 330,719

[22] Filed: Oct. 28, 1994

[51] Int. Cl.⁶ .................................................. H05G 1/00
[52] U.S. Cl. .......................... 378/208; 378/68; 73/864.91
[58] Field of Search ............................. 73/863, 864.91; 378/20, 68, 177, 195, 205, 208; 250/440.11, 442.11; 356/244, 246

[56] References Cited

U.S. PATENT DOCUMENTS

| | | | |
|---|---|---|---|
| 3,627,431 | 12/1971 | Komarniski | 356/244 |
| 3,645,690 | 2/1972 | Rochte et al. | 73/864.91 |
| 4,245,052 | 1/1981 | Lund | 356/246 |

FOREIGN PATENT DOCUMENTS

| | | | |
|---|---|---|---|
| 12241 | 1/1992 | Japan | 73/864.91 |

Primary Examiner—Hezron E. Williams
Assistant Examiner—Nashmiya Ashraf
Attorney, Agent, or Firm—Thorpe North & Western

[57] ABSTRACT

A holder for micro-samples for use with an analysis instrument relying on a beam of radiation or accelerated particles and a method for making the same is disclosed. The holder includes a frame with one or more orifices covered by a thin polymer film. One or more concave impressions are formed in the thin polymer film at the precise positions where samples can be placed to intersect a probe beam during analysis.

11 Claims, 2 Drawing Sheets

THIN FILM SAMPLE SUPPORT

BACKGROUND OF THE INVENTION

The present invention relates to thin polymer films with a concavity which serves as a receptacle to position a sample for chemical analysis. The concavity is drawn in the film by placing an open tube in contact with the film at the desired position and creating a mild vacuum in the tube to stretch the polymer film slightly beyond its elastic limit, or by other suitable means. The resulting concavity remains after the removal of the tube or other forming device.

Various methods of spectral analysis of chemicals (e.g. x-ray fluorescence, XRF) use a cup as a container of liquid samples. Torrisi, in U.S. Pat. No. 4,587,666 (1986), describes a method of making a sample cup with thick walls and a membrane to separate the liquid sample from the vacuum chamber of the XRF instrument. The membrane is large (1 to 2 inches) and must have a "perfectly flat horizontal face." The container can support a liquid or solid and separate it from the vacuum portion of the instrument while passing at least some of the illuminating and emitted radiation.

An alternative method of supporting a sample with a low vapor pressure is to attach it to a thin, flat membrane and support the entire assembly in the vacuum chamber of the instrument. The probe beam can be electromagnetic radiation (e.g. x rays) or particles (e.g. accelerated protons). For small samples, micro-beams (diameters of less than 2 mm) have been used. This puts the support membrane under intense radiation which could lead to damage and failure.

The characteristics of the membrane are important for the analysis in the following ways, a partial list from Solazzi in his article entitled "Xray Fluorescence Thin-Film Sample Support Materials," American Laboratory, (1985), 17(11):3:

1. Relatively high degree of resistance to chemical attack.
2. Resistance to radiation damage such as embrittlement, thermal softening, etc.
3. Good sample retention strength so the dried sample does not fall off or blow off.
4. Freedom from interfering impurities.
5. Thin, and yet strong enough to withstand handling.

Support films typically limit the detection of small quantities of analyte because the films scatter photons or particles from the probe beam. In XRF, scattering is the limiting factor. In response, over the past 40 years workers have attempted (with limited success) to make thinner films of low atomic weight materials (carbon, nitrogen, oxygen, hydrogen and boron). Examples are boron nitride as proposed by Prang, et al., ("Boron Nitride Sample Carriers for Total-Reflection Xray Fluorescence," Spectrochemica Act, (1993), 48B: 153–161), and by Pauwels, et al., ("Polyimide Substrate for Nuclear Targets," Nuclear Instruments and Methods, (1979), 167: 109–112). The thicker the film, the more the film becomes a limiting factor in the analysis. Those skilled in the art will recognize that techniques for preparing thin polymer films (i.e. films of less than about 50 $\mu g/cm^2$) are well known.

Many samples are solutions or suspensions. The solvent is typically evaporated (see Hannson, et al., "A Non-Selective Preconcentration Technique for Water Analysis by PIXE," Nuclear Instruments and Methods in Physics Research, (1984), B3: 158–162 and Mangelson, et al., "Particle Induced X-ray Emission Elemental Analysis: Sample Preparation for a Versatile Instrumental Method," Scanning Microscopy, (1990), 4: 63–72). Flat sample holders are often made of a porous material (e.g. filter paper). Even though the sample droplet may be carefully placed, there remains ambiguity in the position of the sample after drying because of uncontrolled amounts of lateral diffusion and soaking of the solution which has been applied. Even when the film is smooth and impervious to liquid, the small sample may not dry exactly in its initial position because of droplet motion. Slight inhomogeneities in the surface tension of the film may induce the droplet wet and spread in an uncontrollable manner. Additionally, evaporation may deposit the solid at the edge of the evaporating droplet. These processes take an unknown portion of the sample out of the microscopic probe beam, and invalidate the analysis.

Over the past 40 years, a long-felt need has become evident because all of the conventional approaches suffer from one or more of the following problems:

1. The position of the small, dry sample is uncertain (e.g. soaking on filter paper);
2. The sample falls off during handling;
3. The holder deteriorates because of radiation damage or high temperature or both; and
4. Upon drying, the holder allows the sample to clump in such a way that the probe beam and radiation emitted by the analyte do not correctly represent the quantity of sample.

This last problem arises because a large clump can severely attenuate the probe radiation (leaving some of the sample unexcited), or it can attenuate the emitted radiation. In addition, emission of one element in the sample can be absorbed by another and enhance the emission of the second, thus invalidating the analytical method. It is very difficult to correct for these effects from sample to sample because the clump size (and therefore the error) may vary from place to place because of random amounts and positions of clumping. A thin film of the analyte minimizes these errors and allows for a dependable calibration of their extent. The severity of this self-absorption problem scales as the absorption coefficient, so the problem can be largely ignored for highly transparent samples.

It would be advantageous if there were precisely located positions on the film where the sample droplet would remain during evaporation. The films should be free of any interfering contaminants. In addition, the film should hold the dry sample in position during handling and analysis. These and other advantages are achieved with the instant invention which is described in more detail to follow.

SUMMARY OF THE INVENTION

It is an object of the present invention to provide a thin polymer film sample holder which increases the position certainty of the small, dry sample.

It is another object of the invention to provide a thin polymer film sample holder which decreases the risk that a sample may fall off during handling.

It is yet another object of the present invention to provide a thin polymer film sample holder which minimizes sample clumping so that the radiation emitted by the analyte more correctly represents the quantity of the sample.

The above and other objects of the invention are realized in specific illustrated embodiments of a thin film sample support including a thin film (i.e. less than about 50 $\mu g/cm^2$) and a support frame attached to the film so that an upper surface of the film is held generally planar. One or more concave impressions are formed in the film to receive and hold samples during testing. The concave impression in the film supports either a small solid sample, or a small amount of liquid solution (possibly while it dries). The sample is also supported during the time it is in an instrument such as an x-ray fluorescence spectrometer. For a number of instruments, the liquid must be removed before placing the sample in the vacuum environment of the instrument.

In accordance with one aspect of the invention, the concave impressions are formed by applying a negative pressure to the film so that small areas of the film are deformed beyond the film's elastic limits so as to form the concave impressions.

In accordance with another aspect of the invention, the concave impressions are formed by placing a blunt instrument against the film and deforming a small area of the film beyond its elastic limits.

In accordance with yet another aspect of the present invention, material that lumininesces in an irradiating beam is placed in one of many concavities to allow precise alignment in the probe beam.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE INVENTION

Figure 1:
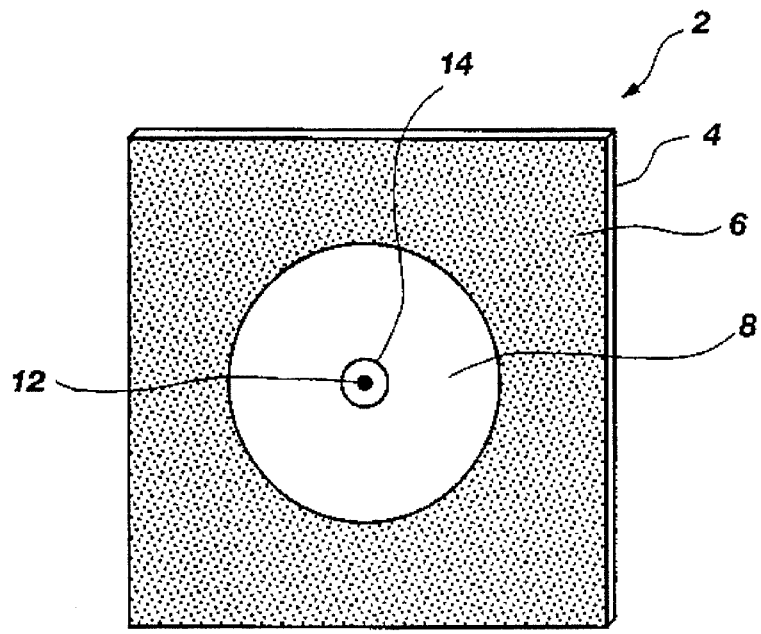
FIG. 1 shows a frame having one surface covered with a thin film that is marked in the center to receive a liquid sample.
Figure 2:
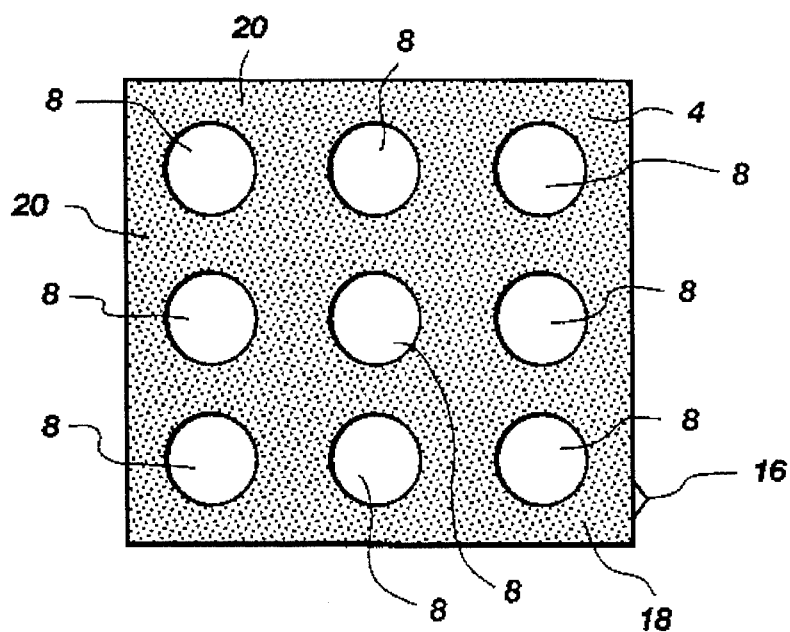
FIG. 2 shows a single frame having nine orifices over which the thin film would be laid.

Reference will now be made to the drawings in which the various elements of the present invention will be given numeral designations and in which the invention will be discussed so as to enable one skilled in the art to make and use the invention. Referring to FIGS. 1 and 2, there is shown a sample holder, generally indicated at 2, for use in analytical instruments where a small amount of analyte must be suspended in an irradiating beam of particles or electromagnetic radiation. The particles are typically electrons, protons, neutrons or alpha particles. The electromagnetic radiation could come from any portion of the spectrum (gamma rays to infrared wavelengths). The invention is especially suited to instruments using micro beams (i.e. beams of very small cross section). The spectrometers most commonly used for quantitative analysis are X-ray fluorescence spectrometers (XRF), proton induced x-ray emission spectrometers (PIXE) and Fourier transform infrared spectrometers (FTIR). The invention is also useful as a support for nuclear targets, nuclear strippers, and filters in more general types of beam experiments.

The sample holder 2 of FIG. 1 includes a frame 4 which supports a thin polymer film 6. The frame 4 circumscribes one or more orifices 8. A sample 12 is placed in a small concave impression 14 positioned above an approximate center of the orifice 8. The orifice(s) 8 are large enough to allow a probe beam of radiation to strike the sample 12 in the concave impression 14 of the film 6, without striking the frame 4. Typically, the concave impression 14 will have a diameter of about 2 mm, while the orifices 8 will have a diameter of about 15 mm. The frame 4 can be made of metal, polymer, ceramic or any solid material with sufficient dimensional stability.

The orifices 8 can be placed for convenience, e.g. to match the sample transport mechanism of the instrument for correct positioning of each sample. Such positioning is aided by reference points 16 (FIG. 2) and reference surfaces 18 (FIG. 2) positioned on the frame 4 to meet the demands of the instrument. Fiducial marks 20 may also be placed on the frame as alignment aids. In the preferred embodiment, a sample of material that lumininesces in the irradiating beam is placed in one a concave impression, such as 14 in FIG. 1, to allow precise alignment in the probe beam. The testing equipment can then automatically know the location of other samples.

For some applications, the frame 4 must not contaminate the vacuum chamber of the instrument by emitting gases or vapors. Additionally, it must not shed particles. Thus, aluminum sheet (1.6 mm thick) is the material of the frame 4 for a preferred embodiment.

Referring specifically to FIG. 2, the top of the frame 4 (or at least each orifice) would be covered with a thin polymer film 6 (FIG. 2) which is preferably less than 50 µg/cm$^2$. Thick films scatter sufficient radiation to degrade the performance of the instrument. So the film must be pure and must be made of light elements (e.g. H, B, C, N, O). Under these conditions, the film is not a source of greater noise than that inherent in the instrument.

The film 6 of the preferred embodiment consists of pure polyimide with thickness in the previously specified range. However, other films may be used, such as polyvinyl formal, polycarbonate, polypropylene, polyethylene, paralene, PROLENE™ (isotactic polypropylene) and MYLAR™. These materials allow an aqueous sample droplet to retain a nearly spherical shape as it dries. The lack of liquid spreading places the sample reliably in the original position of the sample droplet.

An additional feature of such thin polymer films is their micro-flexibility, which gives them the ability to conform to the surface of small particles as they yield to attractive Van der Waals forces. The conformation greatly increases the fraction of particle surface that is in contact with the film, and causes the particles to adhere tenaciously to the film during handling and analysis.

Figure 3:
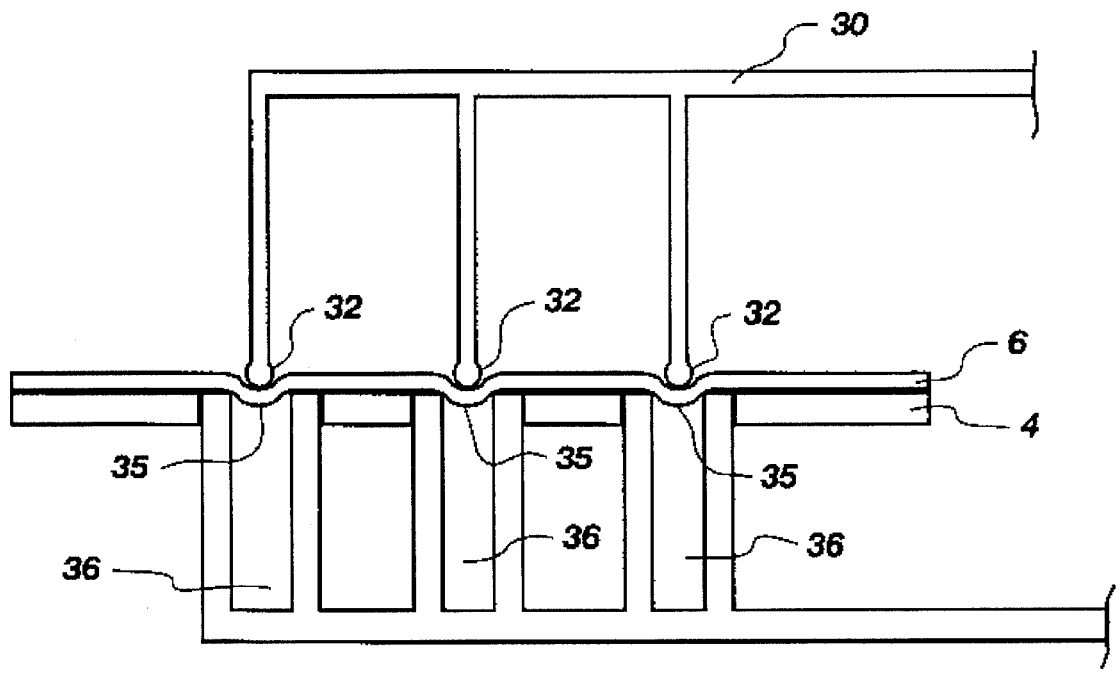
FIG. 3 shows a cross-sectional view of a fixture that creates precisely located concavities in the thin film by application of a blunt instrument.

The film may be marked at the positions where sample droplets are to be placed, or better, a concavity can be created precisely at each intended sample position. As shown in FIG. 3, the concave impressions can be made with a tool 30 having one or more rounded heads 32 of the desired diameter (typically 2 mm). The tool 30 is used to depress the upper surface 34 of the film 6 a little beyond its elastic limit as the film is supported by the open end 35 of one or more tubes 36 with inside diameter larger than the rounded tool. There is danger of tearing the membrane because of concentrating shear forces through slight misalignment of the tube and rounded tool. Accordingly, appropriate measures should be taken to ensure that the imposed force does not exceed the sheer and tensile strength of the polymer.

Figure 4:
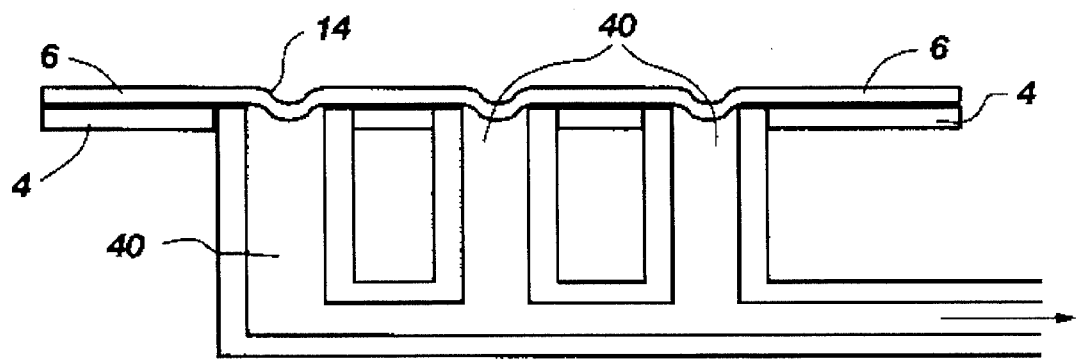
FIG. 4 shows a cross-sectional view of a fixture that creates precisely located concavities in the thin film by application of a mild vacuum.

In the preferred embodiment shown in FIG. 4, the concave impressions are made with only a tube 40 (or with several tubes in a fixture to position them correctly). By applying a mild vacuum in the tubes 40 which are attached to a manifold 42, the concave impressions 14 can be drawn into the film 6. A fixture (not shown) is used to place the tubes in the proper positions relative to the fiducial marks and surfaces of the frame.

In addition to the above methods, the concave impression could also be etched into the thin film. However, because of the thinness of the film, generally less than 50 µg/cm$^2$, it is extremely easy to tear the film. Thus, this is not a preferred embodiment.

While the discussion above generally shows forming the concave impression 14 in the upper surface of the thin film 6, the impression could also be formed in the lower surface. The film may also be rotated so that it extends generally vertically, such as is often the case during testing. Because the sample tends to stick to the liner, the impression could be formed in the lower surface. The appended claims are intended to cover obvious changes in the disposition of the film 6.

The invention and associates improved thin films offer the following important benefits and features:

1. It allows the liquid to dry evenly so the remaining solid sample is homogeneously deposited on the area covered by the liquid;
2. It is made of light, low-fluorescence elements (typically, polyimide comprised of C, H, N, and O) and is free of impurities that would degrade the quality of the analysis;
3. It does not degrade the quality of a hard vacuum by outgassing;
4. It is flat and sufficiently stretched on its frame so there are no intrinsic wrinkles and no sagging under the sample mass and its own mass, even at high radiation flux and/or temperatures;
5. A concavity can be formed at a precise position in the membrane to receive the sample and hold it in the proper position; and
6. The surface of the film interacts spontaneously with the dried sample to keep it from falling off or blowing off during transport and during analysis in the instrument.

Those skilled in the art will recognize other advantages which may be achieved by applying the principles of the present invention to thin films.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

We claim:

1. A sample holder for holding a micro-sample to be subjected to particle beams and beams of X-ray electromagnetic energy, the sample holder comprising:

a thin polymer film having a surface density of less than about 50 µg/cm$^2$ and including a generally planar upper surface and a lower surface, at least one concave impression being formed in the film and sized for receiving the micro-sample to be subjected to X-ray electromagnetic energy, while maintaining nominal scattering of X-rays; and a support frame defining at least one orifice for holding the thin polymer film and maintaining the upper surface in a generally planar orientation, the thin film being disposed on the frame with the concave impression disposed in alignment with the orifice such that an x-ray beam may pass through the impression without contacting the frame.

2. The sample holder of claim 1, wherein the thin polymer film comprises a plurality of concave impressions for receiving samples to be subjected to electromagnetic energy, each concave impression having a diameter.

3. The sample holder of claim 1, wherein the at least one concave impression comprises a plurality of impressions and wherein the support frame comprises a plurality of orifices formed therein such that each orifice is disposed about a concave impression in the thin polymer film, each orifice having a diameter greater than that of an adjacent concave impression.

4. The sample holder of claim 1, wherein the concave impression is formed in the lower surface of the thin film.

5. The sample holder of claim 1, wherein the concave impression is etched into the thin polymer film.

6. The sample holder of claim 1, wherein the lower surface of the thin polymer film is generally planar, and wherein the concave impression is formed in the generally planar upper surface so as to form a generally convex protrusion extending from the generally planar lower surface.

7. The sample holder of claim 1, wherein the film is formed of at least one of the group consisting of polyvinyl formal, polyimide, polycarbonate, polypropylene, polyethylene, paralene, PROLENE and MYLAR.

8. The sample holder of claim 7, wherein the film is formed of polyimide.

9. The sample holder of claim 1, wherein the support frame comprises an aluminum frame.

10. The sample holder of claim 1, further comprising positioning means disposed on the thin polymer film.

11. The sample holder of claim 10, wherein the positioning means comprises a material that luminesces in an irradiating beam disposed in the concave impression of the thin polymer film.

* * * * *

UNITED STATES PATENT AND TRADEMARK OFFICE
CERTIFICATE OF CORRECTION

PATENT NO. : 5,544,218
DATED : Aug. 6, 1996
INVENTOR(S) : Turner, et al.

It is certified that error appears in the above-identified patent and that said Letters Patent is hereby corrected as shown below:

Column 3, Line 19 Delete "lumininesces" and replace therefore --luminesces--

Column 4, Line 17 Delete "lumininesces" and replace therefore --luminesces--

Column 4, Line 18 Delete "one"

Column 4, Line 47 change "Van" to --van--

Column 5, Line 21 change "associates" to --associated--

Signed and Sealed this

Twentieth Day of May, 1997

Attest:

BRUCE LEHMAN

*Attesting Officer*   *Commissioner of Patents and Trademarks*